US00RE35706E

United States Patent [19]

Phillips et al.

[11] E Patent Number: Re. 35,706

[45] Reissued Date of Patent: Dec. 30, 1997

[54] LIPOPHILA DERIVATIVES OF MURAMYLPEPTIDES HAVING PROPERTIES OF ACTIVATING MACROPHAGES AND COMPOSITIONS CONTAINING THEM

[75] Inventors: Nigel Phillips, Pointe Claire, Canada; Françoise Audibert, Neuilly sur Seine, France; Jean-Marie Bernard, Fontenay le Fleury, France; Louis Chedid, Paris, France; Pierre Lefrancier, Gif S/Yvette, France; Michel Level; Monique Parant, both of Paris, France

[73] Assignee: VACSYN Inc., Tampa, Fla.

[21] Appl. No.: 329,142

[22] Filed: Oct. 25, 1994

Related U.S. Patent Documents

Reissue of:

[64] Patent No.: 4,939,122
Issued: Jul. 3, 1990
Appl. No.: 206,959
Filed: Jun. 9, 1988

U.S. Applications:

[63] Continuation of Ser. No. 886,359, May 21, 1992, abandoned, which is a continuation of Ser. No. 96,794, Sep. 15, 1987, abandoned, which is a continuation of Ser. No. 733,529, May 13, 1985, abandoned.

[30] Foreign Application Priority Data

May 11, 1984 [FR] France ..... 84 07340

[51] Int. Cl.[6] ..... A61K 38/14; A61K 38/16; C07K 9/00

[52] U.S. Cl. ..... 514/8; 530/322; 536/53

[58] Field of Search ..... 530/322; 514/8; 536/53

[56] References Cited

U.S. PATENT DOCUMENTS

| | | | |
|---|---|---|---|
| 3,931,139 | 1/1976 | Wissmann et al. | 530/331 |
| 4,101,536 | 7/1978 | Yamamura et al. | 530/322 |
| 4,310,514 | 1/1982 | Durette | 530/322 |
| 4,315,913 | 2/1982 | Durette | 530/322 |
| 4,369,178 | 1/1983 | Yamamura et al. | 530/322 |
| 4,579,840 | 4/1986 | Hahn | 530/328 |
| 4,628,045 | 12/1986 | Hahn | 530/330 |
| 4,672,106 | 6/1987 | Hamaoka et al. | 536/53 |
| 4,681,856 | 7/1987 | Hamaoka et al. | 536/53 |
| 4,683,292 | 7/1987 | Hahn | 530/328 |

FOREIGN PATENT DOCUMENTS

| | | | |
|---|---|---|---|
| 0025495 | 3/1981 | European Pat. Off. | 515/8 |
| 0056992 | 8/1982 | European Pat. Off. | 514/8 |
| 0102319 | 10/1984 | European Pat. Off. | 514/8 |
| 0135788 | 4/1985 | European Pat. Off. | 514/8 |

OTHER PUBLICATIONS

Rose et al., *Cancer Treatment Report*, vol. 66 No. 1, pp. 135–146, 1982.

Long et al., *Cancer Treatment Reports*, vol. 71, No. 6, pp. 593–598, 1987.

Rubin et al., *Cancer Treatment Reports*, vol. 71, No. 5, pp. 489–492, 1987.

*Primary Examiner*—Avis M. Davenport
*Attorney, Agent, or Firm*—Larson & Taylor

[57] ABSTRACT

The invention relates to muramyleptide derivatives resulting essentially from the conjugation or the coupling, as the case may require, through an arm, between a muramylpeptide and a group containing two atoms contiguous with one another to each of which is attached a lipophile chain comprising from 8 to 100 carbon atoms, preferably from 14 to 24 carbon atoms. The derivatives according to the invention are endowed with remarkable stimulating properties with respect to the activation of macrophages, of which they amplify the tumoricidal properties.

22 Claims, No Drawings

LIPOPHILA DERIVATIVES OF MURAMYLPEPTIDES HAVING PROPERTIES OF ACTIVATING MACROPHAGES AND COMPOSITIONS CONTAINING THEM

Matter enclosed in heavy brackets [ ] appears in the original patent but forms no part of this reissue specification; matter printed in italics indicates the additions made by reissue.

CROSS-REFERENCE TO RELATED APPLICATIONS

[This is a continuation of Ser. No. 096,794, filed Sept. 15, 1987 (now abandoned), which was a continuation of Ser. No. 733,529, filed May 13, 1985 (now abandoned).]

*This application is a continuation of Reissue application Ser. No. 07/886,359, filed May 21, 1992 (now abandoned), which is a reissue of U.S. Ser. No. 07/206,959, filed Jun. 9, 1988 (now U.S. Pat. No. 4,939,122), which is a continuation of U.S. Ser. No. 07/096,794, filed Sep. 15, 1987 (now abandoned), which is a continuation of U.S. Ser. No. 06/733, 529, filed May 13, 1985 (now abandoned).*

BACKGROUND OF THE INVENTION

The invention relates to lipophile derivatives of muramylpeptides having properties of activating macrophages, and more particularly, tumoricidal properties. It relates more particularly to compositions containing these lipophile dervatives of muramylpeptides, more particularly compositions based on liposomes or which can form liposomes with which are incorporated said muramylpeptide lipophile derivatives.

The activation of macrophages is one of the principal mechanisms of antitumoral activity of immunomodulators: activated macrophages are capable of destroying syngenic tumoral cells not only in vitro, but also in vivo.

It has also been shown that muramylpeptides could increase the antitumoral activity of macrophages in vitro. It is not the same in vivo when the substances are used in saline solution. This inactivity is doubtless due to the fact that muramylpeptides penetrate slowly into the macrophages, no doubt by fluid pinocytosis and that muramylpeptides are rapidly eliminated from the organism through the kidney. It is then a consequence of these two phenomena that muramylpeptides injected in saline solution do not reach a sufficient concentration in the macrophages to be able to activate them.

Several solutions have been contemplated to overcome these drawbacks. In particular, it has been shown that encapsulation of muramylpeptides in liposomes confers on macrophages a cytotoxic activity already considerable in vitro and in vivo. FIDLER and his collaborators have developed this approach by the use of multilamellar liposomes composed of phosphatidylcholine (PC) and phosphatidylserine (PS) in a ratio 7/3 and including MDP; thus they arrive at targeting this immunomodulator towards circulating monocytes which are differentiated, under the influence of the MDP that they have endocyted, into activated macrophages (Canc. Res., 42, 161–167 (1982)).

The composition of the liposomes and their nature (multilamellar) permit them to be directed, in particular, to the capillaries of the pulmonary circulation. The monocytes which have phagocyted them then migrate into the lung where they are differentiated in activated macrophages; these activated macrophages are capable of destroying metastases of tumors with pulmonary tropism like the $B_{16}$ melanoma in the mouse.

However, the use of soluble muramylpeptides runs up against numerous drawbacks: certain liposomes (in particular those whose composition favours targeting towards the monocytes of the pulmonary circulation) "leak", that is to say they loose the encapsulated solute: this leakage is particularly marked when the PC/PS liposomes are placed in the presence of serum. These leakages naturally prevent good preservation of the liposomes.

This drawback is partly overcome by the use of multilamellar liposomes. It is possible in fact to think that the innermost interlammellar spaces can contain or limit the leakages before the phagocytosis of the liposome. This solution involves however a loss of specificity of targeting. In fact the use of unilamellar liposomes or constituted by few lamellae could present advantages on targeting at other organs than the lung (G. POSTE et Coll., Cancer Res., 42, 1412–1422 (1982).

To overcome this, FIDLER et Coll., have also already recognised the use of lipophile derivatives of N-acetylmuramyl-L-alanyl-D-isoglutamine (MDP), or of N-acetylmuramyl-L-alanyl-D-isoglutamyl-L-alanine (MTP), such as MTP-phosphatidylethanolamine.

It has also been proposed to conjugate MDP or MTP with phosphatidylethanolamine or with a stearic acid molecule, to stimulate the cytotoxic activity of the macrophages. However, the preparation of liposomes containing such derivatives does not proceed without difficulty. In particular, the formation of fine films of lipids containing the muramylpeptide derivatives and the transformation of these fine films of lipids into liposomes by conventional methods does not always lead to reproducible results and the liposomes can scarcely be preserved for prolonged periods.

In addition, it is observed that certain derivatives of muramylpeptides already containing certain lipophile groups, could show toxic and/or destabilising properties with respect to the macrophages.

It is an object of the invention to overcome yet more effectively the difficulties which have been mentioned above, in particular of providing novel MDP derivatives, possessing a considerable capacity of activating macrophages, and more particularly, of their in vivo tumoricidal activity, and this more particularly when they are administered in liposome form.

It is also an object of the invention to provide muramylpeptide lipophile derivatives which can be used among other things in the preparation of liposomes incorporating them, these liposomes then being characterised simultaneously by particularly high properties of stimulating macrophages and by great stability, both as regards the possibilities of storing these liposomes (or of compositions which can easily be transformed into liposomes) and their absence of destabilising or toxic action with respect to macrophages.

GENERAL DESCRIPTION OF THE INVENTION

According to the invention there are provided muramylpeptide derivatives resulting essentially from the conjugation or the coupling, as the case may require, through an arm between a muramylpeptide and a group containing two atoms contiguous with one another, to each of which is joined a lipophile chain comprising from 8 to 100 carbon atoms, preferably from 14 to 24 carbon atoms.

The two contiguous atoms form particularly part of one of the following structures:

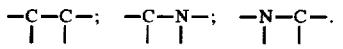

Preferred compounds of the invention are characterised by the following formula:

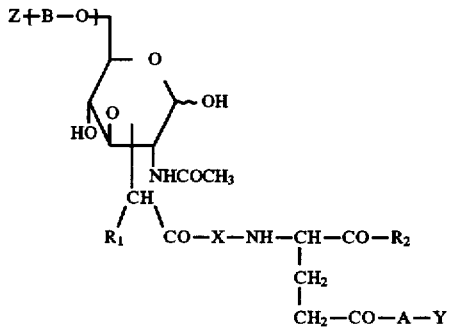

in which the substituents $R_1$, $R_2$, X, Y, A and B have the following meanings:

$R_1$ is H or $CH_3$, $R_2$ is —$NH_2$, —OH group or —[OW]*OD* group, with [W] *D* being a hydrocarbon group comprising from 1 to 10 carbon atoms, X is an aminoacyl residue of the group comprising: alanyl, valyl, isoleucyl, norleucyl, leucyl, seryl, threonyl, prolyl, glutaminyl, asparaginyl, methionyl, tryptophanyl, phenylalanyl, tyrosyl, glycyl.

[Y has the same meaning as $R_2$ or is a lipophile group —$OCH_2$—$CHO(R_3)CH_2O(R_4)$ with $R_3$ and $R_4$, respectively identical or different, being acyl groups comprising from 8 to 100 carbon atoms;

Z has the same meaning as $R_2$ or is a lipophile group —CO—$CHO(R_3)CH_2O(R_4)$ with $R_3$ and $R_4$, respectively identical or different, being acyl groups comprising from 8 to 100 carbon atoms; it being however understood that one at least of the two groups Y and Z is always constituted by the corresponding lipophile group;]

*Y is —$NH_2$, —OH, —OD or a —$OCH_2$—$CH(OR_3)CH_2O(R_4)$ lipophile group in which a hydrogen on a methylene in its glyceryl group may be replaced by a lower alkyl group; $R_3$ and $R_4$ being identical or different and being individually an acyl or alkyl group of 8 to 100 carbon atoms;*

*Z is —$NH_2$, —OH, —OD or a —W—B—CO—$CH(OR_3)CH_2O(R_4)$ lipophile group in which a hydrogen on a methylene in its glyceryl group may be replaced by a lower alkyl group; Y or Z both being a lipophile group;*

*W is —O or —NH—; and*

A and B are either direct linkages, or groups, respectively identical or different, comprising respectively from one to three amino acyl residues, themselves identical or different from one another, or again a —NH—$(CH_2)_p$—CO— group with values of p comprised between 2 and 10.

In the preferred compounds of the invention, the group X is a levogyratory aminoacid residue, (naturally when the aminoacyl residue is other than glycyl). Particularly preferred groups X are L-alanyl, L-seryl, L-valyl, L-leucyl, L-isoleucyl, L-threonyl, or glycyl. Preferably also $R_2$ is constituted by an alkyl-oxy group.

The groups A and B are advantageously constituted by direct linkages, in which case the group Y is directly linked to the gamma-carboxyl of the glutamyl group and in which case the group Z is directly linked to the oxygen atom at the 6 position of the saccharide group. A and B can also be constituted by one or several aminoacyl residues having the meanings indicated for X, preferably L-alanyl and/or L-lysyl.

It goes without saying in the foregoing, that it is possible to resort to any possible combinations employing one or several of the preferred groups which have been mentioned, these groups being combinable, independantly of one another, with the basic muramylpeptide structure modified by the group bearing the two lipophile chains.

One group of compounds is however particularly preferred. It is those in which:

the group Z is constituted by the corresponding lipophile group, as defined above, and in which $R_2$ is an alkyl-oxy group comprising from 1 to 10 carbon atoms, and more particularly 4 carbon atoms, especially n-butyl-oxy, A is direct linkage and Y is an $NH_2$ group.

These latter types of compounds are particularly remarkable in that they are practically devoid of any pyrogenicity.

The lipophile groups $R_3$ and $R_4$ particularly preferred are constituted by palmitoyl groups.

The invention relates more particularly to compositions of liposomes or easily convertible into liposomes and containing one or several compounds according to the invention. The incorporation of the compounds according to the invention with liposomes results in fact in a considerable exaltation in their stimulation activity with regard to macrophages.

It is to be noted that the presence of two lipophile groups on two continuous carbon atoms of the glyceryl group contributes to the anchorage of the muramylpeptide on or in the lipid walls of the liposomes and comes into play essentially at the level of the stability of the liposomes themselves and of the absence of toxic or destabilising effect with respect to macrophages entering into contact with them. Such are at least the observations which can be made in both in vitro and in vivo tests.

Although it is not indispensable it is possible to use, to constitute the liposomes, lipids characterised by a transition temperature Tm higher than 37° C. This transition temperature is related to the average temperature of transition between the "solid crystal" state and the "liquid crystal" state, in which said lipids can exist, particularly in liposome membranes, at temperatures respectively less than and greater than this temperature Tm. The use of liposomes characterised by a temperature Tm higher than 37° C. favors the exclusive targeting of the macrophages. It is from the aspect that phospholipids formed from fatty acids comprising in their chain from 14 to 30, particularly from 16 to 24 carbon atoms, are preferred.

As regards lipids employed to form liposomes (or compositions suitable to form liposomes), it is possible to refer to the technical literature which is abundant in this field. Preferred lipid compositions are those which bring into play phospholipids, such as phosphatidylcholine (a derivative of fatty acids comprising from 12 to 20 carbon atoms) (particularly from 16 to 20 carbon atoms), phosphatidylserine, phosphatidylinositol, phosphatidylethanolamine, phosphatidylglycerol, and phosphatidic acid. These phospholipids can be used alone or in mixtures. It is more particularly advantageous to resort to mixtures of synthetic or natural distearylphosphatidylcholine (DSPC) or phosphatidylcholine and of phosphatidylserine (PS) or of phosphatidylglycerol (PG). Advantageously, the liposomes are formed from mixtures containing the last mentioned phospholipids in a ratio of 7 volumes of DSPC or phosphatidylcholine (PC) to 1 to 10, preferably 3, volumes of PS. The biological activities of the liposomes containing the derivatives of the invention are manifested as well when the liposomes are in the unilamellar or plurilamellar form. Preferably, the particles of liposomes have sizes greater than or equal to 0.1 micron, for example, comprised between 1 and 10 microns.

Preferably, the compounds according to the invention are used in liposomes or suspensions of these liposomes in physiologically acceptable aqueous solutions, preferably sterile and isotonic, when these compositions are intended to be administered parenterally.

It is advantageous for the liposome suspension to comprise from 4 to 400 micromoles of lipids and from 20 to 200 micrograms of the muramylpeptide lipophile derivatives according to the invention per milliliter of medium.

The invention relates more particularly also to liposome compositions with which are incorporated lipophile derivatives of muramylpeptides in the lyophilised state, consequently perfectly anhydrous. It has in fact been noted that the lyophilisation of such preparations of such liposomes resulted, after extemporaneous formation of a liposome suspension, in a considerable increase in the stimulating activity of the macrophages. These anhydrous lyophilised compositions can be preserved for several months, in the absence of any loss of activity.

The preparation of the product according to the invention can be done from muramic acid, from its analogs or from its derivatives, which have in common the structure called below "muramic structure":

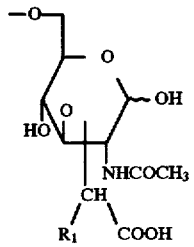

in which $R_1$ has the previously indicated meaning.

Preferred methods of preparing the compounds according to the invention comprise the fixation of the peptide chain of formula X—D—Glu—(A—Y)—$R_2$, in which X, A and Y have the above-indicated meanings on the muramic structure by traditional methods in the field of peptide synthesis and, as the case may require, the fixation of the —B—Z group at the 6—0— position of the muramic structure. It is then understood that the functions borne by the partners of the reaction, and which do not take part in the latter, will have previously been protected if necessary. The protected functions are finally liberated in the terminal phases of the preparation of the compounds of the invention. The methods described in the prior literature and in particular in the French patent applications whose references are recalled below, can also be applied to the production of the compounds according to the invention.

The substitution $R_2$ is advantageously performed on the glutamyl group before the synthesis of the chain. In the same way, the group Y is preferably first fixed to the C-terminal aminoacyl before the latter is integrated into the peptide chain.

The peptide syntheses are carried out by traditional methods. By way of example, it is possible to select the methods of activation of the carboxyls, as the activated ester method or that called mixed anhydride method, or indeed that using a compound of the carbodiimide type, such as N, N-dicyclohexylcarbodiimide or equivalent carbodiimides. A review will be found of the conventional methods of peptide synthesis in J. H. JONES, Chemistry and Industry, 723 (1974). Reference may also be made to the French patent applications already mentioned, or again to the following applications: n* 75 29624, 76 06819, 76 06820, 76 06821, 76 21889, 77 02646, and to the articles of LEFRANCIER et al. (Int. J. Peptide Protein Res., 1977, 9, 249 and 1978, 11, 289 and J. Med. Chem. 25, 1982, 87).

The formation of the esterified or amide derivatives corresponding to the group $R_2$ is obtained in known manner. Reference may be made in particular to the French patent applications mentioned above, and particularly to applications n* 76 06820, 76 06821, 76 21889 and 77 02646.

When the group Y must be formed by a glycerol group, carrying two lipophile chains, it is obtained by esterification of the gamma-carboxyl function, as the case may require activated, of the glutamic group or (when A does not constitute a direct linkage) of the C-terminal aminoacyl, by a glycerol itself bêta, gamma-diesterified by chains of lipophile acids, particularly fatty acids, this glycerol bearing none the less a free terminal hydroxyl function. The N-terminal function of the peptide chain will generally have been protected, prior to the esterification reaction, for example by a t-butyl-oxy-carbonyl (BOC) group. Reference may also be made to French patent n* 78 08049, in which are also described methods of preparation of peptide chains modified by a glycerol group, itself bearing other groups. These methods of preparation are also applicable to the preparation of modified peptide chains which can be employed for the preparation of the compounds according to the present invention. Thus, the synthesis of the peptide sequence bearing the di-substituted lopophile group can be accomplished.

The synthesis of the corresponding muramylpeptide derivative is then completed by coupling with the muramic structure of the peptide chain (modified or not, as the case may be, by the di-substituted glycerol group) after prior liberation of the N-terminal amine function. This muramic structure will have itself been protected previously. It will, for example, be constituted by alpha-O-benzyl-4,6-O-benzylidene-N-acetyl-muramic acid. The glycopeptide derivatives are finally obtained in the free state, after elimination (by hydrogenolysis, for example) of the protective groups.

Another method of preparation consists of coupling directly the alpha substituted derivative (by an amide or an ester, according to the general formula) of N-acetyl-muramyl-L-alnayl-D-glutamic acid with the previously prepared H-A-Y group, for example, but without limitation, by using the mixed anhydrides method.

The derivatives according to the invention in which the B—Z— group comprises a glycerol-bêta group gamma-diesterified by lopophile acids, particularly fatty acids, can then be obtained by reaction of the above-said glycopeptide derivatives—before elimination of the protective groups at the 1, 4 and 6 positions of the saccharide group—with the corresponding gamma-diesterified bêta glyceric acid.

Other characteristics of the invention will appear also in the course of the description which follows, of one of its preferred examples, there being no intended limitation therein.

DESCRIPTION OF PREFERRED EMBODIMENTS

EXAMPLE I:

Synthesis of alpha (N-acetyl-muramyl-L-alanyl-D-isoglutamine), beta, gamma-dipalmitoyl-sn-glycerol (MDP-GDP)

of formula:

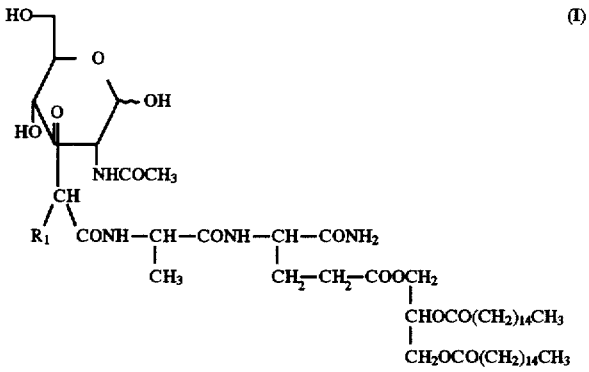

(I)

alpha-(BOC-L-Ala-D-isoGln), beta, gamma-dipalmitoyl-m-glycerol

To a solution, in 10 ml of THF-DMF (1/1) of 119 mg (0.375 mM) of BOC-L-Ala-D-isoGln, 142 mg (0.25 mM) of beta, gamma-dipalmitoyl-sn-glycerol and 180 mg (0.406 mM) of BOP, are added 0.05 ml (0.406 mM) of N-methylmorpholine and 31 mg (0.45 mM) of imidazole. After a weekend at room temperature, the product is extracted in chloroform, then purified on a column of 20 g of 60 G silica, stabilised in chloroform, then eluted with successively chloroform (100 ml), the mixture chloroform-methanol; 50/1 (100 ml), then 25/1. After ultrafiltration of its solution in chloroform, (I) is lyophilised from its solution in dioxane: 73 mg (33.6%) $[\alpha]_D^{25}$: 0° (c: 0.5 glacial acetic acid)

Anal. Calc. for $C_{48}H_{89}N_3O_{10}$%: C: 66.4; H: 10.3; N: 4.8. Found: C: 66.2; H: 10.2; N: 4.3.

alpha-(L-Ala-D-isoGln), bêta, gamma-dipalmitoyl-sn-glycerol, HC 1 (II)

521 mg (0.6 mM) of (I) are treated by 1.6 ml of a normal solution of hydrochloric acid in glacial acetic acid, for 45 minutes, at ambiant temperature. (II) is obtained, after concentration of the solvent, by lyophilisation of its solution in acetic acid and used immediately: 480 mg.

alpha-MurNAc-(alpha-OBzl-4,6-O-Bzi)-L-Ala-D-isoGln, bêta, gamma-dipalmitoyl-sn-glycerol (III)

378 mg (0.47 mM) of (II), 260 mg (0.55 mM) of MurNAc (alpha-O-Bzl-4,6-O-Bzi), 265 mg (0.605 mM) of BOP 0.2 ml (1.75 mM) of N-methylmorpholine are dissolved in 8 ml of chloroform-DMF (5/2). After 36 hours, the product is extracted with chloroform and purified on a silica column stabilised in the mixture chloroform methanol (15/1), then eluted with the mixture of the same solvents (12/1). After ultrafiltration of its solution in chloroform, (III) is lyophilised from its solution in acetic acid: 545 mg (95%). [alpha] $_D^{25}$: +40° (c: 0.5, glacial acetic acid).

Anal. Calc. pour $C_{66}H_{108}N_4O_{15}$, 0.5 $CH_3COOH$ %: C: 66.2 H: 8.8; N: 4.5.

Found: C: 66.4; H: 8.7; N: 4.3.

alpha(MurNAc-L-Ala-D-isoGln), bêta, gamma-dipalmitoyl-sn-glycerol (IV)

535 mg (0.44 mM) of (III) are hydrogenated in solution in 30 ml of glacial acetic acid, in the presence of 550 mg of 5% Pd on charcoal, for 40 hours. After filtration of the catalyst, (IV) is obtained by lyophilisation from its solution in acetic acid, then purified on a silica column eluted by the mixture chloroform-methanol (5/1). After ultrafiltration of its solution in chloroform, (IV) is lyophilised from its solution in glacial acetic acid: 348 mg (72.2%). $|alpha|_D^{25}$: +23.4° (c: 0.7; glacial acetic acid).

Anal. Calc. for $C_{54}H_{98}N_4O_{15}$ 1.6 $CH_3COOH$: %: C: 60.29; H: 9.23; N: 4.92.

Found: %: C: 60.3; H: 9.2; N: 5.0.

EXAMPLE II:

synthesis of 6-O-(bêta, gamma-dipalmitoyl-L-glyceryl)-N-acetyl-muramyl-L-alanyl-D-glutamine-n-butyl-ester (6-O-GDP-MDPG-OnBu) of formula

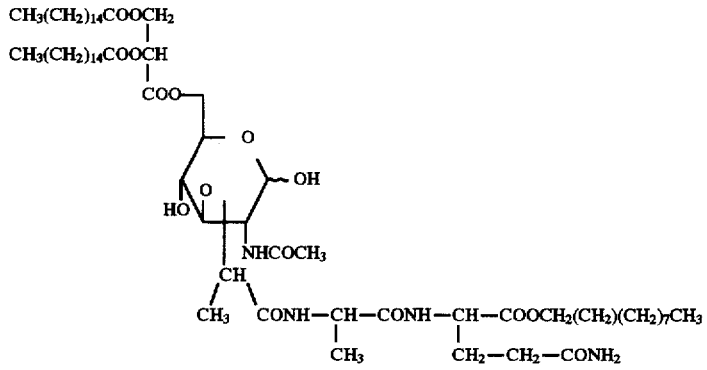

(I)

L-glycerate benzyl-ester

To 222 mg (0.2 mM) of glyceric acid, are added 463 mg (2 mM) of diisopropylbenzylisouree. After 3 hours stirring at room temperature, 5 ml of anhydrous and deperoxydised THF were added; after 24 hours at room temperature, the solution was cooled to −15° C. and the diisopropylurea was removed by filtration. (I) is obtained after purification on the silica column in the mixture chloroform-methanol-acetic acid (120/10/1): 316 mg (80%). $[alpha]_D^{25}$: −16.6° (c: 0.55; dioxanne). SpectrumIR: 3410–3510 $cm^{-1}$ (OH); 1735 $cm^{-1}$ (ester). SpectrumU.V.: 252 nm, 257 nm, 262 nm (benzyl).

bêta, gamma-dipalmitoyl-L-glycerate benzyl ester (III)

316 mg (1.6 mM) of (I) are dissolved in 3 ml of drying pyridine. At 0° C. and under a current of argon, was added, in 15 minutes, a solution in 6 ml of dry dichloromethane of 1.382 g (4.83 mM) of palmitoyl chloride. After 4 hours reaction at room temperature, 80 ml of dry ether were added, then 60 ml of iced 0.5N $H_2SO_4$. After 20 minutes stirring, the organic phase was washed until neutral pH, dried over $Na_2SO_4$, filtered and concentrated. (II) is obtained after purification on a silica column in the mixture hexane-ethyl acetate (8/2): 835 mg (77.5%).

M.P: 39°–40° C. $[alpha]_D^{25}$: −11.5° (c: 1; chloroform).

Anal. Calc. for $C_{42}H_{72}O_6$: %: C: 74.95; H: 10.78.

Found: %: C 75.2; H: 10.6.

Bêta, gamma-dipalmitoyl-L-glyceric acid (III)

750 mg (11.1 mM) of (II) were hydrogenated in 20 ml of THF, in the presence of 300 mg of 5% Pd on charcoal. After 3 hours, the solution was ultrafiltered, then concentrated until the production of a powder: 520 mg (80%). $[alpha]_D^{25}$: −6.35% (c: 0.4; chloroform).

Anal. Calc. for $C_{35}H_{66}O_6$: %: C: 72.12; H: 11.41.

Found %: C: 72.0; H: 11.5.

6-O-(bêta, gamma-dipalmitoyl-L-glyceryl-1-alpha-benzyl-N-acetyl-muramyl-L-alany-D-glutamine-OnButyl ester (IV)

To a solution in 3 ml of DMF, 658 mg (1.2 mM) of MurNAc (alpha-Bzl)-L-Ala-D-Gln-OnBu, were added 233 mg (0.4 mM) of (III), 50 mg (0.4 mM) of 4-dimethylaminopyridine, 64 mg (0.4 mM) of N-hydroxybenzotriazole, 95 mg (0.46 mM) of DCC. After the addition of 1.5 ml of dry dichloromethane, the reaction mixture was left under stirring for 24 hours at room temperature, then supplimented with 150 ml of chloroform. The organic phase was washed with 0.5M HCL,M $NaHCO_3$ and then with water, dried over $Na_2SO_4$ and concentrated. (IV) was first precipitated in absolute ethanol, and purified on a silica column, eluted successively by the mixture chloroform-methanol-acetic acid (18/1/0.1), by the mixture chloroform-acetic acid (5/1), then finally by methanol. After ultrafiltration of its chloroform solution, (IV) is obtained after concentration: 330 mg (69%).

M.P: 157°–162° $[alpha]_D^{25}$: +46° (c: 0.5; acetic acid).

Anal. Calc. for $C_{65}H_{110}N_4O_{16}$ 0.5 $H_2O$: %: C: 64.38; H: 9.23; N: 4.62.

Found: %: C: 64.3; H: 9.1; N: 4.4.

6-O-(bêta-gamma-dipalmitoyl-L-glyceryl)-N-acetyl-muramyl-L-alanyl-D-glutamine-OnButyl ester (V)

120 mg (0.1 mM) of (IV), dissolved in 15 ml glacial acetic acid and 1 ml of methanol, were hydrogenated in the presence of 120 mg of 5% Pd of charcoal for 20 hours. After filtration of the catalyst, (V) was lyophilised from its solution in glacial acetic acid: 107 mg (96%). $[alpha]_D^{25}$: +15.4° (c: 0.4, glacial acetic acid).

Anal. Calc. for $C_{58}H_{104}N_4O_{16}$ 1 $CH_3COOH$: %: C; 61.41; H: 9.28; N: 4.77.

Found: %: C: 61.5; H: 9.0; N: 4.8.

EXAMPLE III:

Synthesis of alpha (N-acetyl-muramyl-D-alanyl-D-isoglutamine), bêta, gamma-dipalmitoyl-sn-glycerol (MDP (D-D) - GDP).

The method of synthesis is the same as that used in the preparation of MDP - sn GDP.

The product obtained has the following analytical characteristics: $(alpha)_D^{25}$=+31.5° (c=0.5 glacial acetic acid)

Anal. Calc. for $C_{54}H_{98}N_4O_{13}$, 1$CH_3$ COOH (1103 546): %: C: 60.95: H: 9.31: N: 5.07.

Found %: C: 60.68: H: 9.22: N: 5.17.

EXAMPLE IV:

Synthesis of alpha (N-acetyl-muramyl-L-alanyl-D-isoglutaminyl-L-alanine), beta, gamma-dipalmitoyl-sn-glycerol (MDP - L Ala - GDP).

The process of synthesis is indicated below along its main lines. The product obtained has the following analytical characteristics: $(alpha)_D^{25}$=+15.6° (c=0.3 glacial acetic acid)

anal. Calc. for $C_{57}H_{103}N_5O_{16}$, 2$CH_3$ COOH (1234 59): %: C: 59.34; H: 9.06: N: 5.67.

Found %: C: 59.46: H: 9.04: N: 5.99.

EXAMPLE V:

Synthesis of alpha (N-acetyl-muramyl-D-alanyl-D-isoglutaminyl-L-alanine) beta, gamma-dipalmitoyl-sn-glycerol (MDP (D - D) - L Ala - GDP). (alpha)= +25.7° (c=0.35 glacial acetic acid)

Anal. Calc. for $C_{57}H_{103}N_5O_{16}$, 1.5 $CH_3COOH$ (1204 56): %: C: 59.82; H: 9.12; N: 5.81.

Found %: C: 59.75; H: 9.05; N: 6.06.

For the two latter derivatives, the method of synthesis is as follows: preparation of BOC-L-Ala-gamma-dipalmitoyl-sn-glycerol, esterification being done under the conditions described previously for the preparation of alpha-BOC-L-Ala-D-isoGln-gamma-dipalmitoyl-sn-glycerol, by use of the pair of coupling reagents (BOP - imidazole).

The group BOC is then removed conventionally and the product obtained is coupled by using the coupling reagent BOP, with either MDP, or MDP (D - D). Thus, there is finally obtained, after a first purification on a silica column, eluted with chloroform-methanol 5/1, then after a second purification on a LH 20 column, eluted with chloroform methanol 1/1, either MDP-L-Ala-GDP, or MDP (D - D) L-Ala-GDP.

EXAMPLE VI:

Synthesis of 6-O-(beta, gamma-dipalmitoyl-L-glycerol)-capryl-N-acetyl-muramyl-L-alanyl-D-glutamine-n-butyl ester (6-O-GDP-aminocapryl-MDPG-OnBu).

PREPARATION OF LIPOSOMES:

(a) Preparation of multilamellar liposomes

PC or DSPC and PS (in the molar ratios respectively of 7:3, 7:0.3, or 7.0) were mixed with MDP-GDP, in a solution of anhydrous chloroform. The solution is introduced into a round-bottomed glass flask, subjected to rotary stirring and simultaneously to evaporation. The film of anhydrous lipids formed on the inner surface of the flask is cooled with a solution of sodium chloride buffered with PBS phosphate at 20° C. for 10 minutes, the suspension being then subjected to vigourous stirring at 60° C. in a device called VORTEX, to form liposomes. The relative proportions of MDP-GDP with respect to the phospholipids and the relative proportions of the PBS buffer with respect to the lipids were each time selected so as to obtain in the final liposomes relative proportions of phospholipids and of MDP-GDP, with respect to the volumes of the suspension used, which are indicated in the tables of results indicated below. Liposomes containing MDP were produced under the same conditions, in order to make comparisons.

Finally, the control liposomes were prepared in the same manner, and in the absence of MDP-GDP.

(b) Preparation of lyophilised liposomes

Lyophilised liposomes were prepared by dissolving DSPC, PS and MDP-GDP in suitable proportions in anhydrous 2-methyl-2-propanol at 28°–30° C. Aliquot parts containing the relative amounts of constituents indicated in the tables of results which follow (in a total volume of 1 ml) were placed in flasks suitable for lyophilisation. After freezing the solutions of 2-methyl-2-propanol at +4° C., the flasks were subjected to lyophilisation for 6 hours at 20° C. The lyophilised lipid compositions were preserved at –20° C. or +4° C. in sealed flasks until the time of use. The preparation of liposomes from these lyophilised compositions can be carried out at any time by the addition of the required volume of PBS buffer at 60° C., the suspension then being subjected to vigorous stirring in a VORTEX device for 2 minutes, then preserved in an ice bath for 30 minutes before the performance of the tests.

The liposomes containing the MDP-GDP have a remarkable stability compared with that of liposomes made with MDP. Liposomes produced under the same conditions, but with muramylpeptides labeled with tritium have enabled the following observations. Retention tests of the muramylpeptide in the liposomes suspended in an MEM-FCS medium (mixture of "minimum essential medium containing Searle salts" and foetal calf serum) have shown that more than 50% of the MDP incorporated had been lost after 4 hours of incubation at 37° C. and that more than 80% of the MDP had been lost after 18 hours of incubation. On the contrary, the MDP-GDP of the corresponding liposomes had been preserved almost entirely. The incorporation of the MDP-GDP and the stability of the latter, has also been verified in reaction tests with anti-MDP monoclonal antibodies. After incubation of these liposomes in the same medium at 37° C. for 72 hours, there is observed a constant agglutination of the liposomes with the antibody (95% of the liposome being agglutinated), this observation bearing witness to the practical absence of any loss of MDP-GDP. It has in fact been shown that the MDP part of the muramylpeptide was externalised on the liposomal membrane. The leakage, if it was produced, would have been manifested by a decrease in the intensity of agglutination with time. In addition, analysis of the N-acetylmuramyle sugar by the Morgan-Elson method has demonstrated the absence of leakage after incubation of these liposomes at 37° C. for 72 hours.

Quite similar observations have been made with liposomes prepared with 6-O-GDP-MDPG-OnBu or with the products of Examples III, IV, V and VI.

The invention therefore relates very particularly to lyophilised liposomes in powder form which can at any moment be resuspended in a suitable buffer solution, by shaking in a VORTEX device for a very short time, particularly for 2 minutes. In the tests which follow, reference will often be made to the employment of the "lyophilised liposomes". It goes without saying that this expression relates to liposomes previously resuspended under the above indicated conditions, particularly in a PBS buffer.

The invention relates more particularly again to lyophilised liposomes of this type which retain from 20 to 2,000 micrograms of lipophile muramylpeptides according to the invention per 4 to 400 micromoles of lipid. Preferably, the lipids are themselves constituted by a mixture of DSPC and PS, in which the ratio DSPC/PS varies from 7:1 to 7:10, particularly is of the order of 7:3.

BIOLOGICAL TESTS

(1) TESTS OF CYTOTOXIC ACTIVITY IN VITRO INVOLVING MEDIATION OF MACROPHAGES

The target cells used in these tests were constituted by cell cultures of B16-BL6 mouse melanoma, kept in monolayers, syngenic for C57B1/6 mice.

The macrophages used were alveolar macrophages of F344 male rats of 200 g. The macrophages were obtained by washing lung with 9×5 ml of DULBECCO PBS medium, without calcium or magnesium, from rats anesthetized with 0.5 ml 5% Nembutal ip (Abbott Laboratoires S. A.) and bled through a canula placed in an artery of the kidney. After centrifugation, the macrophages were resuspended in MEM (minimal essential medium) containing Earle's salts (marketed by "Flow Laboratories S.A.") supplemented with 5% of inactivated foetal calf serum, glutamine, sodium pyruvate, unessential amino acids, vitamins and antibiotics (penicillin and streptomycin).

The suspension was then adjusted to $5\times10^5$ macrophages/ml and distributed in the proportion of 100 microliters per cup in a Titertek 76-002-05 plastic dish. After incubation for 4 hours at 37° C., in an atmosphere containing 5% $CO_2$, the macrophages adhered to the walls of the cups. The non-adherent cells were then removed by through washing with MEM-FCS medium. The macrophage monolayers were then incubated with the liposome preparations, with non-liposomic MDP and control liposomes contained in a final volume of 200 ml for 24 hours. The macrophage monolayers were then washed three times, each time with 200 microliters of MEM-FCS medium per cup.

In addition, B16-BL6 target cells in expontential growth phase, were incubated in the presence of 0.2 microcuries/ml of $125_I$—OdUrd (specific activity 2200 curies/mMole) for 24 hours. The monolayers were then washed thoroughly with serum-free MEM to remove any unincorporated $125_I$—IdUrd The cells were then detached by treatment for 1 minute with a trypsin solution (0.25%)/EDTA (0.02% in PBS. The detached cells were then suspended in MEM-FCS medium. After washing by centrifugation at 800 g for 10 minutes at 4° C., the cells were resuspended in MEM-FCS medium to obtain a concentration of viable cells of $5\times10^4$/ml.

Aliquots (100 microliters of this suspension) were introduced into the cups in contact with pretreated macrophage monolayers and a coculture was carried out during periods of 72 and/or 96 hours respectively. The covering efficiency of the B16-BL6 cells were shown to be of the order of 90–95%.

At the end of the incubation period, each cup was washed three times with 200 microliters of heated PBS and the remaining adherent cells were lysed by the addition of 200 microliters of 0.5M NaOH. The lysate and the washings from each cup were combined and introduced into the tank of a liquid scintillation counter. All the determinations were carried out in triplicate. This specific cytotoxicity in % was calculated by using the following formula:

$$\frac{\left[\begin{array}{c}\text{Mean count } (CPM)\\ \text{on target cells +}\\ \text{control macrophages}\end{array}\right] - \left[\begin{array}{c}\text{Mean Count } (CPM)\\ \text{on target cells +}\\ \text{treated macrophages}\end{array}\right]}{\left[\begin{array}{c}\text{Mean count } (CPM)\\ \text{on target cells +}\\ \text{control macrophages}\end{array}\right]} \times 100$$

It is to be noted that this test rests on the proportion of DNA of the B16-BL6 cells which is liberated in the medium by lysis of said cells, when the latter are killed by the macrophages (or unliberated as regards surviving B16-BL6 cells).

The results of these tests appear in the Table I. Here are indicated the results of the residual radioactivity of the treated cells under the above-indicated conditions (CPM ± standard deviation (SD)) cytotoxicated in % (values appearing between parenthesis in Table I).

In the left hand portion of the table appear also the concentrations of MDP or of the MDP-GDP per milliliter of liposome suspension or of saline solution, as regards the free MDP.

The same tests were carried out with liposomes retaining MDP-GDP reformed from "lyopilised liposome" preparations. The results are shown in Tables II and III. The following observations are derived from examinations of these three tables.

Table I shows that the MDP liposomes exert a sensitizing activity with respect to macrophages 700 times higher than free MDP. However, the liposomes of MDP-GDP (evaluated in MDP equivalents) are 7,000 times more active than free MDP and consequently 10 times more active than the liposomes of MDP (Table 1). However, the lyophilised liposomes of MDP-GDP (Tables II and III) are considerably mopre active still since, at equal doses, the lyophilised liposomes liposomes of MDP-GDP have a stimulant activity 500,000 times higher than free MDP (values expressed with respect to MDP equivalent doses of MDP-GDP retained in the liposomes). The stimulating effect of the macgrophages is particularly great when the cocultures have been conducted for 96 hours.

This cytotoxicity, conjugated with the very great stability of the liposomes, therefore reveals a quite remarkable importance, especially if it is remembered that the lyophilised liposomes, in powder form, can be preserved for several months without loss of activity.

(2) IN VIVO TESTS (a) In situ activation of alveolar macrophages obtained from mice to which had been administered lyophilised liposomes containing MDP-GDP and in vivo distribution of the liposomes containing MDP-GDP and 6-0-GDP-MDGP-OnBu.

Lyophilised liposomes containing 10 micrograms of MDP-GDP or of 6-0-GDP-MDPG-OnBu in a volume of 200 microliters of PBS were injected into the vein of the tail of C57B1/6J mice. The aveolar macrophages were collected 24 hours later under the above-described conditions, by washing lungs from the animals. After washings with MEM-FCS buffer, the macrophages were measured into the cups of microplates ($5\times10^4$ macrophages per cup) and B16-BL6 melanomas cells labeled with [$125_I$]-Id-Urd were added. The cytotoxic activities were measured under the above described conditions.

Similar tests were carried out with control liposomes and liposomes containing MDP. The results are shown in Table IV, which table shows that the macrophages obtained from animals which had received liposomes of MDP-GDP or of 6-0-GDP-MDPG-OnBu possess a considerable cytotoxic activity with respect to B16-BL6 cells, whilst macrophages obtained from animals which had received control liposomes or liposomes with which had been incorporated MDP, were revealed to possess only a very slightly increased cytotoxic activity with respect to that of macrophages obtained from untreated animals.

(b) Distribution of the lyophilised liposomes in the organs.

These tests were carried out by injection into the animals, under conditions similar to those which have been indicated above, of liposomes retaining MDP-GDP, but whose DSPC had been labeled with carbon 14.

Four hours after the injection, the animals were sacrificed and the lungs, the liver and the spleen were taken out. The percentage of radioactivity retained at the level of these organs and also of the blood was evaluated. These measurements were done with different relative proportions of DSPC and of PS. The results are shown in Table V, which reveals that the presence of substantial amounts of PS shows that the relative increase of the proportions of PS with respect to the DSPC favours a pulmonary localization of the liposomes adsorbed in vivo. The molar ratio DSPC/PS of 7:3 gives particularly favourable results. This is the ratio which has been used in the test which follows.

(c) In situ effects of lyophilised liposomes retaining MDP-GDP on metastases induced experimentally in the mouse by B16-BL6 cells.

B16-BL-6 tumoral cells in the exponential growth phase were collected by trypsinisation, washed by centrifugation and resuspended in PBS to provide suspensions containing $5\times10^5$ viable cells per milliliter. 0.2 ml of this suspension was injected into a lateral vein of the tail of C57B1/6J mice. Each mouse was treated intravenously with 200 microliters of a solution of 0.5 micromole of the abovesaid lyophilised liposomes retaining 10 micrograms of MDP-GDP at days 3, 5, 7, 9 and 12 after the day of injection of the tumor cells. At day 21, the mice were killed by cervical dislocation and the number of pulmonary metastases was recorded under a dissection microscope.

Animals were treated by control liposomes devoid of MDG-GDP.

The effect of the treatment on the number of metastases was analysed by employing the MannWhitney "u" test.

The results are shown in Table VI. Here there is indicated in particular the average numbers of pulmonary metastases noted in the various groups of animals treated on day 21 following the injection of B16-BL6 cells.

The result show that lyophilised liposomes based on MDP-GDP can induce a vary substantial reduction of metastases, whilst control liposomes or similar doses of free MDP are without effect on the development of the metastases observed in the controls.

Examination of the sizes of the residual metastases after treatment reveals that the metastases of diameter less than 2 mm were completely eradicated. Only larger metastases subsisted having a size greater than 2.5 mm.

This being the case, it will be observed that the liposomes according to the invention show a particularly effective activity against metastases, especially if a count is taken of the observations which were made by KEY M.E. et Coll. (J. Natl. Canc. Inst., 69:1189–1198, 1982) that metastases having sizes greater than 1 mm were not affected by treatment with liposomes retaining MDP.

The results obtained in vivo with representative compounds of the class of compounds according to the invention are also quite superior to those which have been obtained, under similar conditions with liposomes of MTP-phophatidyl-mono-ethanolamine. The latter shown in fact in the same tests, an activity of the same order of magnitude as the liposomes based on MDP.

It is also interesting to note that the products of the invention show a maximum activity after 96 hours, whence a duration of action at the level of the metabolism which compares favourably also with that of comparison molecules, whose action is much more rapid.

Certain of the compounds according to the invention show at relatively high doses, a certain pyrogenicity, whose impact is however reduced, taking into account the particularly higher therapeutic index from which they appear to benefit. This being the case, the muramylpeptides in which the group of modification by the two lipophile chains is fixed to the 6 position of the saccharide group, and of which the peptide chain is terminated by a glutamy-alpha-ester-gamma-amide group, are particularly advantageous by reason of their more reduced pyrogenicity. Testimony thereof is borne by comparative pyrogenicity measurements carried out on groups of three rabits with the two compounds more particularly studied, according to the procedure of the European Pharmacopoea, Vol. 2, 1971, pages 58–60. In fact, the following results are obtained, expressed by temperature observations observed in experimental animals to which had previously been administered 1 mg/kg of the compounds studied: for the MDP-GDP : 1°;0.9° and 1° C.; for the 6 -0-GDP-MDPG-OnBu : 0.2°; 0.3° and 0.5° C.

The results obtained with representatives of the class of compounds according to the invention show that the introduction of two lipophile chains, respectively jointed to two contiguous atoms of a carrier group coupled to a muramylpeptide makes the latter particularly suitable, especially when it is placed in the form of liposomes, to activate macrophages and confer on them a high antitumoral activity. It is to be noted also that the lipophile derivatives of muramylpeptides according to the invention have also preserved the characteristic properties of MDP, that is to say, adjuvant and at the same time, anti-infectious properties (particularly with respect to Klebsiella).

In particular, the adjuvant activity of MDP(GDP) and of 6-0-GDP-MDPG-OnBu has been tested in the Swiss female mouse. At day 0, 100 micrograms of C474 were injected with 500 micrograms of bovine serumal-bumin. At day 30, the animals received a booster of 100 micrograms of antigen alone. The following results were obtained:

| | Primary response 1.21 | Secondary response 1.36 | |
|---|---|---|---|
| Controls | 1.64 | 5.09 | 2 |
| MDP | 3.97 | 8.48 | 1.7++ |
| MDP-GDP | 3.64 | 10.27 | 0.52++ |
| 6-0-GDP-MDGP-OnBu | 2.64 | 8.6 | 0.71++ |

++p < 0.01

The titers are expressed in Log 2 of the passive hemagglutination titer. At day 21, the serums were titrated in pools; at day 36, they were titrated separately.

The anti-infectious activity (high as is concluded from the results which follow) has been demonstrated by administration of the suspension of $10^4$ cells of Klebsiella pneumoniae, by intravenous injection in 6 to 8 week old Swiss mice. In the Tables VII to XI are indicated the conditions in which the substances were administered and, according to the considered cases, the number of mice surviving 10 or 15 days later and the corresponding percentages of protection with respect to controls.

The observations made may be summarised as follows:

(1) The three products MDP-GDP, MDP (D,D)-GDP and GDP-MDPG-OnBu have a protective activity comparable with respect to infection by lethal doses in the mouse of Klebsiella pneumoniae.

(2) Similar results were observed with MDP-L-Ala-GDP and 6-0-GDP -aminocaproyl-MDPG-OnBu.

(3) When they were injected into liposomes, MDP-GDP is the most active (at 0.1 microgram), but the two others are nonethless more effective (at 10 micrograms) than when they are injected in aqueous suspension.

(4) As with MDP, it is possible to demonstrate a synergic effect with an antibiotic (gentamicin).

(5) MDP(D,D)-L-Ala-GDP, although active, is less so than MDP-L-Ala-GDP.

(6) The experiments carried out with Candida show that MDP-GDP is active, that this effect is increased by incorporation in liposomes, and that it can be added to that of Fungizone (Amphotericine B).

The results obtained against the latter micro-organism result from the tables which follow.

The invention therefore relates to biological reagents which can be constituted by means of the compounds according to the invention. These reagents are useful as reference compounds or for comparison for the study of the activation properties of the macrophage of compounds to be studied, more particularly with respect to their tumoricidal properties with, particularly, pulmonary localisation.

The invention also relates to medicaments containing by way of active principle, at least one of the components according to the invention, these medicaments being applicable as stimulating agents, in the subject to which they are administered, of the activation of macrophages. A particularly preferred field of application is that of the treatment of tumoral diseases and of the prevention of the proliferation and metastases of tumors. However, the field of application of the medicaments according to the invention extends also to the treatment of any infectious diseases, and in particular against pathogenic germs which have become resistant to antibiotics. Finally, the lipophile muramylpeptides according to the invention can also be employed as adjuvants of the immunity induced in a host by an immunogenic agent, particularly a vaccine active principle, and this more particularly when the immunogenic agent is weak. Reference can be made to the text of the prior patents mentioned above, as regards the particular conditions in which these adjuvants can be used.

The medicaments according to the invention can be administered to a host - animal or human being - in any manner suitable for obtaining the desired effect.

The invention relates naturally also to the various pharmaceutical compositions, more particularly based on liposomes bringing into action physiologically acceptable lipids, in which the compounds according to the invention can be incorporated, as the case may require, in association with other active substances.

Advantageous pharmaceutical compositions are constituted by suspensions of injectable liposomes containing an effective dose of at least one compound according to the invention. Preferably, these suspensions are produced in an isotonic sterilized aqueous phase, preferably saline or glucosed.

The invention relates more particularly to such suspensions which are suitable for administration by intradermal, intramuscular or subcutaneous, intravenous injection or again by scarification.

The invention relates also to pharmaceutical compositions, preferably in the form of liposomes, administrable by other routes, particularly orally or rectally, or again in form intended to come into contact with mucous membranes, particularly the ocular, nasal, pulmonary or vaginal mucous membranes.

Consequently, it relates to pharmaceutical compositions in which one at least of the compounds according to the invention is associated with solid or liquid pharmaceutically acceptable excipients, adapted to the constitution of oral, ocular or nasal administrative forms, or with excipients adapted to the constiution of rectal administrative forms, or again with excipients adapted for vaginal administration, for example, gelatinous. They may relate finally to compositions intended for the pulmonary route, particularly solutions prepared for administration by means of a conventional aerosal device.

By way of examples of doses which can be administered, to reinforce the antitumoral defenses of the host, will be mentioned doses of 10 to 10,000 micrograms per kg bodyweight, for example from 50 to 500 micrograms/kg when the administration is performed parenterally, or again, of a dose of 1 to 10 milligrams per kg bodyweight, orally. These doses are expressed in MDP-GDP equivalents included in the liposomes.

These compositions can also be used to perform intralesionnal injections into tumors of the mammary tumor type, melanomas and other solid tumors.

The invention is not limited obviously to the embodiments described above by way of examples, and the man skilled in the art can introduce therein modifications without however departing from the scope of the appended claims.

In particular, the claims which follow relate also to any products which constitute equivalents of those which have been more particularly defined. Under this title, equivalents are constituted by any compounds in which the coupling between the muramylpeptide and the group containing the two above said contiguous atoms, to each of which is joined a lipophile chain as defined above, would be formed differently from those which have been more particularly envisaged. By way of example, the coupling could be effected at the level of the 1 position of the saccharyl group of the muramylpeptide. Similarly, the equivalents of the claimed compounds would be constituted by those compounds in which the coupling would be formed through another arm, for example, through an aminoalcohol residue (—NH—CH—$CH_2$—O) or the like, or again, for example, at the level of the modified peptide chain, through a bridiging group forming an ester linkage with the gamma-carboxyl of the glutamyl residue and joined at its other end to the glyceryl group bearing lipophile chains by any suitable method of linkage. Reference may be made, for example, to French patent No. 78 08049 for which the constitution of other arms and methods which could be applied to form the couplings envisaged within the scope of the present invention. Conversely, there will also be considered as equivalents the compounds of the muramylpeptide in which, for example, the glycerol group bearing the two lipophile chains would be joined directly or indirectly to a —NH— group, itself directly connected to the carbon 6 of the saccharide group of the muramylpeptide.

It goes also again without saying that there would not be outside the scope of the claims, any modified muramylpeptides comprising the same characteristic elements, but which only differ from those which have been more particularly envisaged by local substitutions of groups not specifically envisaged in the definitions which have been given. For example, equivalents of the modified muramylpeptides of the invention would be those which included substituent groups at the 1 position of the saccharide group, for example phenylamino group or substituent groups at the 4 position of the saccharide group, for example acyl groups comprising 1 to 4 carbon atoms. Also would be considered as equivalents of the claimed compounds, those in which the first aminoacyl residue and/or the second aminoacyl residue of the modified peptide chain would be N-substituted, for example by a lower alkyl group, more particularly methyl, or again those compounds in which a hydrogen atom, belonging to one of the methylene groups present in the glutamyl group and/or, as the case may be, the glyceryl group, would itself by replaced by a lower alkyl, for example methyl. The same observations extend to muramylpeptides according to the invention, in which the groups $R_3$ or $R_4$ would be alkyl groups instead of being acyl groups, etc . . .

In conclusion, it should be stressed that these various substitutions would not place the compounds thus modified outside the scope of the invention, as long as they would not modify the essential properties of the muramylpeptides so obtained, particularly as regards their capacity to activate macrophages and to stimulate their in vivo tumoricidal activity.

Antiviral activity of the compounds according to the invention especially of MDP-GDP.

The antiviral activity of this molecule was evaluated in an experimental infection system of the mouse by influenza virus. The experimental protocol included the administration of MDP-GDP by different routes, particularly per os at the dose of 0.1 mg per mouse and subcutaneously at the same dose. The infection of the mice (Swiss mice aged 10 weeks) was carried out by intranasal inoculation of 50 microliters of an influenza virus suspension APR/8 at 1/10,000. The MDP-GDP was given either 24 hours before infection (D-1), or 24 hours afterwards (D+1). The antiviral activity was judged by comparing on the 21st day after infection, the number of animals surviving in the treated groups with respect to that of the group of untreated controls.

At the dose used, an antiviral activity of MDP-GDP was demonstrated as preventive after administration both orally (56% survival) and subcutaneously (44% survival).

These results lead one to think that doses of the compounds according to the invention, which can be used in human clinical practice are within a range running from 0.01 mg/kg to 0.5 mg/kg. As regards the modalities of presentation of the molecule one must retain in particular its use in aqueous or oily suspension, in an oil emulsion or in association with liposomes.

TABLE I

Action of muramylpeptides incorporated in liposomes on the cytotoxic activity of macrophages

| Treatment of macrophages[a] | Residual radioactivity, CPM ± SD (cytotoxicity %)[b] |
|---|---|
| No treatment, cells | |
| Bl6–BL6 alone | 2218 ± 87 |
| MEM-FCS | 2257 ± 155 |
| Control liposomes | 2179 ± 79 (3.5) |
| Liposomes-MDP 1.0 μg/ml[c] | 1290 ± 87 (43) $p < 0.001$ |
| Liposomes-MDP 0.1 | 1483 ± 275 (34) $p < 0.05$ |
| Liposomes-MDP 0.008 | 1897 ± 323 (16) |
| Liposomes-MDP-GDP 1.0 μg/ml | 336 ± 99 (85) $p < 0.001$ |
| Liposomes-MDP-GDP 0.1 | 893 ± 164 (61) $p < 0.001$ |
| Liposomes-MDP-GDP 0.01 | 1674 ± 115 (26) $p < 0.01$ |
| MDP 100 μg/ml[d] | 1501 ± 103 (34) $p < 0.01$ |
| MDP 33 | 1629 ± 313 (28) $p < 0.05$ |
| MDP 11 | 1725 ± 225 (24) $p < 0.05$ |
| MDP 3.8 | 1876 ± 144 (17) $p < 0.05$ |

[a] $5 \times 10^4$ macrophages contained in a volume of 200 microliters were pretreated with DSPC/PC (80 mmoles of phosphilipids), the liposomes of the DSPC/PS containing MDP or MDP/GDP, or free MDP, for 24 hours.
[b] The cytotoxic activity was determined after 96 hours of coculture of the macrophages and $5 \times 10^3$ target cells Bl6–BL6, labeled with [$125_I$]-1dUrd.
[c] Concentrations of MDP-GDP in liposomes.
[d] Concentrations of free MDP.

TABLE II

Action of lyophilised liposomes containing MDP-GDP on the cytotoxic activity of macrophages

| Treatment of macrophages[c] | Residual radioactivity, CPM ± SD (% cytotoxic)[b] 72 hours | 96 hours |
|---|---|---|
| No treatment, cells | | |
| Bl6–BL6 alone | 2562 ± 82 | 2331 ± 103 |
| MEM-FCS | 2752 ± 126 | 1945 ± 217 |
| Control liposomes | 2626 ± 94 (5) | 1877 ± 160 (3.5) |
| Liposomes-MDP-GDP 18.0 μg/ml[c] | 1838 ± 168 (32) $p < 0.001$ | 370 ± 112 (81) $p < 0.001$ |
| Liposomes-MDP-GDP 0.9 | 1756 ± 48 (36) $p < 0.001$ | 312 ± 67 (84) $p < 0.001$ |
| Liposomes-MDP-GDP 0.09 | 1222 ± 52 (56) $p < 0.001$ | 310 ± 83 (84) $p < 0.001$ |
| Liposomes-MDP-GDP 0.009 | 2094 ± 338 (24) $p < 0.05$ | 856 ± 149 (56) $p < 0.01$ |
| MDP 500 μg/ml[d] | 1348 ± 113 (52) $p < 0.001$ | 606 ± 153 (69) $p < 0.001$ |
| MDP 100 | 1870 ± 288 (32) $p < 0.01$ | 1034 ± 141 (47) $p < 0.01$ |
| MDP 10 | 2540 ± 148 (11) $p < 0.05$ | 1055 ± 37 (45) $p < 0.01$ |
| MDP 1 | 2650 ± 208 (4) | 1259 ± 284 (35) $p < 0.05$ |
| MDP 0.1 | 2662 ± 100 (3) | 1428 ± 88 (26) $p < 0.05$ |

[a]$5 \times 10^4$ macrophages contained in a volume of 200 microliters, were pretreated with DSPC/PS liposomes (80 mmoles of phospolipides), liposomes of DSPC/PC containing MDP/GDP, or free MDP, for 24 hours.
[b]The cytotoxic activity was determined after 72 hours or 96 hours of coculture of macrophages and $5 \times 10^3$ target cells Bl6–BL6 labeled with [125$_I$]-1dUrd.
[c]Concentrations of liposomes and MDP-GDP.
[d]Concentrations of free MDP.

TABLE III

Influence of the concentration of MDP-GDP in lyophilised liposomes containing it on the induction of cytotoxic activity of macrophages

| Treatment of macrophages[c] | Residual radioactivity, CPM ± SD (% cytotoxicity)[b] Content of liposomes in phospholipids in mmoles per milliliter 400 | 40 |
|---|---|---|
| No treatment, cells | | |
| Bl6–BL6 | 2076 ± 202 | 1962 ± 134 |
| MEM-FCS | 2214 ± 198 | 1986 ± 36 |
| Control liposomes | 2042 ± 56 (8) | 1900 ± 98 (4) |
| Liposomes MDP-GDP 18.0 μg/ml[c] | 420 ± 168 (81) $p < 0.001$ | |
| Liposomes MDP-GDP 0.9 | 494 ± 202 (78) $p < 0.001$ | |
| Liposomes MDP-GDP 0.09 | 228 ± 202 (90) $p < 0.001$ | |
| Liposomes MDP-GDP 0.009 | 416 ± 32 (81) $p < 0.001$ | |
| Liposomes MDP-GDP 1.8 μg/ml | | 824 ± 162 (63) $p < 0.001$ |
| Liposomes MDP-GDP 0.09 | | 1170 ± 182 (41) $p < 0.01$ |
| Liposomes MDP-GDP 0.009 | | 1662 ± 112 (16) $p < 0.01$ |
| Liposomes MDP-GDP 0.0009 | | 1940 ± 46 (1) |

[a]$5 \times 10^4$ macrophages contained in a volume of 200 microliters pretreated with liposomes DSCP/PS (80 or 8 mmoles phospholipids), or liposomes of DSPC/PC containing MDP-GDP, for 24 hours.
[b]Cytotoxic activity was determined after 96 hours of coculture of the macrophages and $5 \times 10^3$ Bl6–BL6 target cells labeled with [125$_I$]-1dUrd.
[c]Concentrations of liposomes and MDP-GDP.

TABLE IVa

1st and 2nd series of experiments Activation in situ of alveolar macrophages of the mouse by lyophilised liposomes containing MDP-GDP or 6-0-GDP-MDGP-OnBu

| Treatment in situ[a] | Residual radioactivity, CPM ± SD (% cytotoxic) |
|---|---|
| 1st Experiment | |
| No treatment, cells Bl6-BL6 only | 2032 ± 160 |
| PBS | 2019 ± 119 |
| Control liposomes | 1876 ± 200 (7) |

TABLE IVa-continued

1st and 2nd series of experiments Activation in situ of alveolar macrophages of the mouse by lyophilised liposomes containing MDP-GDP or 6-0-GDP-MDGP-OnBu

| Treatment in situ[a] | Residual radioactivity, CPM ± SD (% cytotoxic) |
|---|---|
| Control liposomes + MDP | 1973 ± 94 (2) |
| Liposomes MDP-GDP | 1134 ± 103 (44) p 0.001 |
| 2nd Experiment | |
| No treatment, cells, Bl6–BL6 only | 1638 ± 126 |

TABLE IVa-continued

1st and 2nd series of experiments Activation in situ of alveolar macrophages of the mouse by lyophilised liposomes containing MDP-GDP or 6-0-GDP-MDGP-OnBu

| Treatment in situ[a] | Residual radioactivity, CPM ± SD (% cytotoxic) |
|---|---|
| Liposomes-6-0-GDP-MDPG-OnBu | 1364 ± 116 (33) $p < 0.01$ |
| Control liposomes + MDPG-OnBu | 1606 ± 151 (2) |

Groups of C57B1/6 mice were treated with liposomes of DSPC/PC (0.5 μmole of phospholid: DSPC/PS: molar ratio of 7:3), DSPC/PS liposomes with 10 μg of MDP or DSPC/PS liposomes containing respectively 10 μg of MDP-GDP and 6-0-GDP-MDPG-OnBu, each time in a volume of 200 μl, through a lateral vein of the tail. The alveolar macrophages were collected 24 hours later. After deposit in a layer of $5 \times 10^4$ of macrophages, $5 \times 10^3$ Bl6–BL6 cells labe led with [$125_j$]-1dUrd were added. The cytotoxicity induced by the macrophages was determined after 96 hours of coculture.

The control liposomes + MDPG-OnBu were inactive; there is no value for p.

TABLE IVb

3rd series of experiments Activation in situ of alveolar macrophages of the mouse by liposomes containing MDP ± GDP, 6-0-GDP-MDGP-OnBu or of MDP(DD)-GDP

| Treatment in situ[a] | Residual radioactivity, (PM ± SD (% cytotoxicity)) |
|---|---|
| No treatment, cells | |
| Bl6–BL6 only | 2360 ± 109 |
| PBS | 2301 ± 89 |
| Control liposomes | 2279 ± 153 (4) |
| Control liposomes + MDP | 2306 ± 65 (2) |
| Control liposomes + MDPG-OnBu | 2294 ± 128 (2) |
| Control liposomes + MDP (DD) | 2257 ± 149 (4) |
| Liposomes - MDP-GDP | 1534 ± 123 (35) $p < 0.001$ |
| Liposomes - 6-0-GDP-MDPG-OnBu | 1770 ± 137 (25) $p < 0.01$ |
| Liposomes - MDP(DD)-GDP | 1416 ± 119 (40) $p < 0.001$ |

[a]Groups of C57B1/6 mice were treated with liposomes of DSPC/PC (0.5 μmole of phospholipid: DSPC/PS: molar ration of 7:3), DSPC/PS liposomes mixed with 10 μg of MDP or DSPC/PS liposomes containing respectively 10 μg of MDP-GDP and 6-0-GDP-MDPG-OnBu, each time in a volume of 200 μl, through a lateral vein of the tail. The alveolar macrophages were collected 24 hours later. After deposit in a layer of $5 \times 10^4$ of macrophages, $5 \times 10^3$ Bl6–BL6 cells labeled with [$125_j$]-1dUrd were added. The cytotoxicity induced by the macrophages was determined after 96 hours of coculture.

TABLE V

Distribution of lyphilised liposomes containing MDP-GDP[a] in the organs

| DSPC/PS (molar ratio)[b] | % retention of phospholides[c] lung | liver | spleen | blood |
|---|---|---|---|---|
| 7:3 | 8.6 ± 1.4[d] | 45.0 ± 8.4 | 2.4 ± 0.1[d] | 2.9 ± 1.3 |
| 7:0.3 | 1.2 ± 0.1 | 37.3 ± 5.0 | 2.0 ± 0.2[d] | 3.9 ± 0.8 |
| 7:0 | 1.4 ± 0.2 | 42.3 ± 1.6 | 1.6 ± 0.1 | 4.3 ± 1.6 |

[a]Groups of 5 C57B1/6 mice received by injection into a lateral vein of the tail DSPC/PS liposomes labeled with carbon 14 (0.5 μmole of phospholipid) containing MDP-GDP (10 μg) in a volume of 200 μl. The mice were sacrificed in 4 h later and the percentage retention of the label 14C was determined.
[b]Molar ratio of DSPC to PS used for the preparation of the liposomes.
[c]Retention of the label 14C is expressed as percentage of label per organ. The results for whole blood are expressed at % of radioactive label per ml of blood.
[d]Significant difference with respect to the DSPC liposomes (molar ratio 7:0), p less than 0.05.

TABLE VIa

Action of lyophilised liposomes containing MDP-GDP on Bl6–BL6[a] metastases

| Treatment[b] | Number of mice | Average number of pulmonary metastases (range) |
|---|---|---|
| Controls (PBS) | 15 | 31 (19–42) |
| Control liposomes | 8 | 33 (18–50) |
| Liposomes-MDP-GDP, 10 μg | 8 | 8 (2–14) $p < 0.001$[d] |
| MDP, 10 μg | 8 | 35 (22–53) |

[a]Groups of C57B16 mice received by injection into a lateral vein of the tail $10^5$ Bl6–BL6 cells at day 0.

[b]Control DSPC/PS liposomes (0.5 μmole of phospholipid) DSPC/PS liposomes containing 10 μg of MDP-GDP or 10 μg of free MDP in a volume of 200 μl of PBS were injected, through a lateral vein of the tail, days 3, 5, 7, 9 and 12 after the day 0 of the injection of the Bl6–BL6 cells.

[c]The number of pulmonary metastases was determined at day 21 after injection of Bl6–BL6 cells.

[d]Significant difference with respect to the control mice (Mann-Whitney "u" test).

TABLE VIb

Action of liposomes containing MDP-GDP, 6-0-GDP-MDPG-OnBu or PDP(DD)-GDP on Bl6–BL6 metastases

| Treatment[a] | Number of Mice | Average number of pulmonary metastases (interval) |
|---|---|---|
| Controls (PBS) | 10 | 67 (40–98) |
| Confrol liposomes | 9 | 73 (45–108) |
| Liposomes MDP-GDP | 9 | 31 (21–40) $p < 0.01$ |
| Liposomes 6-0-GDP-MDPG-OnBu | 9 | 42 (18–70) $p < 0.05$ |
| Liposomes MDP(DD)GDP | 9 | 18 (12–33) $p < 0.001$ |

[a]Groups of C57B1/6 mice were treated with liposomes of DSPC/PS (0.5 μmoles of phospholipid: DSPC/PS: molar ratio of 7:3), DSPC/PS liposomes mixed with 10 μg of MDP or DSPC/PS liposomes containing respectively 10 μg of MDP-GDP and 6-0-GDP-MDPG-OnBu, each time in a volume of 200 μl, through a lateral vein of the tail. The alveolar macrophages were collected 24 hours later. After deposit in a layer of $5 \times 10^4$ of macrophages. $5 \times 10^3$ Bl6–BL6 cells labeled with [$125_j$]-1dUrd were added. The cytotoxicity induced by the macrophages was determined after 96 hours of coculture.

TABLE VII

PROTECTIVE ACTION OF MDP-GDP AND OF ITS DERIVATIVES INJECTED AS AN AQUEOUS SUSPENSION IN THE MOUSE INFECTED BY *KLEBSIELLA PNEUMONIAE*

| Treament at day - 1 (i;v.) | Survival (15 d) | Protection (%) |
|---|---|---|
| Controls | 1/56 | |
| MDP 100 μg | 30/56 | 52 |
| MDP-GDP 100 μg | 32/48 | 65 |
| Controls | 0/32 | |
| MDP 100 μg | 15/32 | 47 |
| MDPG-OnBu 100 μg | 20/32 | 62.5 |
| 6-0-GDP-MDPG-OnBu 100 μg | 22/32 | 68.7 |
| Controls | 0/24 | |
| MDP 100 μg | 12/24 | 50 |
| MDP(D,D) 100 μg | 5/24 | 20.8 |
| MDPG(D,D)-GDP 100 μg | 20/24 | 83.3 |

Mice infected (intravenously) with $10^4$ *k. pneumoniae*

TABLE VIII

PROTECTIVE ACTION OF MDP-GDP AND OF ITS DERIVATIVES INCORPORATED IN LIPOSOMES IN THE MOUSE INFECTED BY *KLEBSIELLA PNEUMONIAE*

| Treatment at day - 1 (i.v.) | | Survival (15 d) | Protection (%) |
|---|---|---|---|
| Liposomes | | 20/24 | |
| Liposomes MDP-GDP | 0.01 μg | 6/16 | 31.2 |
| | 0.1 μg | 18/24 | 66.7 |
| | 1 μg | 18/24 | 66.7 |
| | 10 μg | 20/24 | 75 |
| Liposomes | | 2/24 | |
| Liposomes | | | |
| 6-0-GDP-MDPG-OnBu | 1 μg | 8/24 | 25 |
| | 10 μg | 15/24 | 54 |
| Liposomes | | 2/24 | |
| Liposomes | | | |
| MDPG(D,D)-GDP | 1 μg | 4/24 | 8 |
| | 10 μg | 14/24 | 50 |

Mice infected intravenously with $10^3$ *K. pneumoniae*

TABLE IX

INCREASE OF THE PROTECTIVE EFFECT AGAINST *KLEBSIELLA PNEUMONIAE* BY THE ASSOCIATION OF MDP OR MDP-GDP WITH A WEAK DOSE OF ANTIBIOTIC

| Treatment at day - 1 | Survival (15 d) | Protection (%) |
|---|---|---|
| Controls | 0/24 | |
| Gentamicin | 5/24 | 21 |
| MDG 30 μg | 1/24 | 4 |
| MDP + Gentamicin | 14/24 | 58 |
| MDP-GDP 30 μg | 4/24 | 16 |
| MDP-GDP + gentamicine | 14/24 | 58 |

Mice infected intraveously with $5 \times 10^4$ *K. pneumoniae* Gentamicin 10 μg subcutaneously 2 hours after infection. MDP or MDP-GDP 30 μg intravenously 24 hours before infection N.B. In these experiments the infection was produced with a higher number of bacteria than usual to provide a situation where the MDP has only a weak action.

TABLE X

PROTECTIVE ACTION OF OTHER PRODUCTS OF THE SERIES GDP IN THE MOUSE INFECTED BY *KLEBSIELLA PNEUMONIAE*

| Treatment at day - 1 (i.v.) | Survival (15 d) | Protection (%) |
|---|---|---|
| Controls | 2/16 | |
| MDP-L-Ala-GDP | 12/16 | 63 |
| Controls | 2/16 | |
| MDP(D,D)-L-Ala-GDP 100 μg | 6/16 | 25 |
| Controls | 0/16 | |
| 6-0-GDP-aminocaproyl-MDPG-OnBu 100 μg | 9/16 | 56 |

Mice infected intravenously with $10^4$ *K. pneumoniae*

TABLE XI

ASSOCIATION OF MDP-GDP WITH AMPHOTERICIN B

| Treatment | Survival (10 d) | Protection |
|---|---|---|
| Controls | 0/16 | |
| Amphotericin B 3 μg | 2/16 | 13 |
| MDP-GDP 100 μg/day/4 days | 2/16 | 19 |
| MDP-GDP + Amphotericin B | 11/16 | 69 |

TABLE XI-continued

ASSOCIATION OF MDP-GDP WITH AMPHOTERICIN B

| Treatment | Survival (10 d) | Protection |
|---|---|---|
| MDP(D,D)-GDP 100 μg/day/4 days | 0/16 | |
| MDP(D,D)-GDP + Amphotericine B | 3/16 | 19 |

Mice infected by the venous route with $2 \times 10^6$ *Candida albicans:* the MDP-GDP is injected intravenously in the proportion of 100 mg/day for 4 days (−4, −3, −2 and −1); amphotericine B 3 μg is injeccted subcutaneously on the day of infection.

TABLE XII

PROTECTIVE ACTION OF MDP-GDP AGAINST INFECTION BY *CANDIDA ALBICANS.*

| Treatment (days −4, −3, −2, and −1) | Survival (10 d) | Protection |
|---|---|---|
| Controls | 0/8 | |
| MDP-GDP in aqueous suspension (100 μg × 4) | 6/8 | 75% |
| MDP-GDP in liposomes (10 μg × 4) | 5/8 | 62.5% |
| MDP-GDP in liposomes (30 μg × 4) | 6/8 | 75 |

Mice infected by venous route with $10^6$ *Candida albicans*

We claim:

1. A muramylpeptide of the formula:

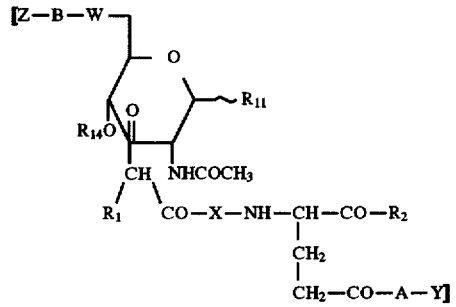

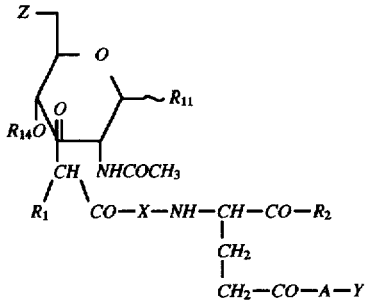

wherein:

$R_1$ is —H or —$CH_3$;

$R_2$ is —$NH_2$, —OH or —OD, with D being a hydrocarbon group of 1 to 10 carbon atoms;

$R_{11}$ is [—H or a phenylamino groups] —*OH*;

$R_{14}$ is —H or an acyl group of 1 to 4 carbon atoms;

X is an aminoacyl residue which is selected from the group consisting of alanyl, valyl, isoleucyl, norleucyl, leucyl, seryl, threonyl, prolyl, glutaminyl, asparaginyl, methionyl, tryptophanyl, phenylalanyl, tyrosyl and glycycl and which may be N-substituted by a lower alkyl group;

Y is —$NH_2$, —OH, —OD or a [—$OCH_2$—$CHO(R_3)CH_2O(R_4)$] —$OCH_2$—$CH(OR_3)CH_2O(R_4)$ lipophile group in which a hydrogen on a methylene in its glyceryl group may be replaced by a lower alkyl group; $R_3$ and $R_4$ being identical or different and being individually an acyl or alkyl group of 8 to 100 carbon atoms *and D is as defined above*;

Z is —$NH_2$, —OH, —OD or a [—CO—CHO($R_3$)$CH_2$O($R_4$)] —*OCO—CH*($OR_3$)$CH_2O$($R_4$), lipophile group in which a hydrogen on a methylene in its glyceryl group may be replaced by a lower alkyl group; Y or Z or both being a lipophile group *and D is as defined above*;

[W is —O— or, when Z is a lipophile group, —NH—; and]

A [and B are] *is* either *a* direct linkage[s] or *a* bridging arm[s] which [are identical or different and which] comprises [individually] one to three aminoacyl residues, themselves identical or different from one another, said aminoacyl residues being selected from the group consisting of alanyl, valyl, isoleucyl, norleucyl, leucyl, seryl, threonyl, prolyl, glutaminyl, asparaginyl, methionyl, tryptophanyl, phenylalanyl, tyrosyl and glycyl and which may be N-substituted by a lower alkyl group, or a —NH—$(CH_2)_2$—O— group;

a hydrogen on a methylene in a glutamyl group of said muramylpeptide being replaceable by a lower alkyl group.

2. The muramylpeptide of claim 1 wherein X is a levogyratory aminoacyl residue or is glycyl.

3. The muramylpeptide of claim 2 wherein X is L-alanyl, L-seryl, L-valyl, L-leucyl, L-isoleucyl, L-threonyl or glycyl.

4. The muramylpeptide of claim 1 wherein A [and B are] *is* L-alanyl or L-lysyl.

5. The muramylpeptide of claim 1 wherein $R_2$ is an alkoxy group.

6. The muramylpeptide of claim 1 wherein A [and B are] *is a* direct linkage[s], Z is a lipophile group, and $R_3$ and $R_4$ are acyl groups.

7. The muramylpeptide of claim 6 wherein $R_2$ is alkoxy of 1 to 10 carbon atoms and Y is —$NH_2$.

8. The muramylpeptide of claim 7 wherein $R_2$ is alkoxy of 4 carbon atoms.

9. The muramylpeptide of claim 8 wherein $R_2$ is n-butoxy.

10. The muramylpeptide of claim 6 wherein $R_3$ and $R_4$ are palmitoyl groups.

11. The muramylpeptide of claim 10 which is 6-O-(beta, gamma-dipalmitoyl-L-[gylceryl]*glyceryl*)-N-acetyl-muramyl-L-alanyl-D-glutamine-n-butyl ester.

12. The muramylpeptide of claim 10 which is 6-O-(beta, gamma-dipalmitoyl-L-glyceryl)-capryl-N-acetyl-muramyl-L-alanyl-D-glutamine-butyl ester.

13. The muramylpeptide of claim 1 wherein A [and B are] *is a* direct linkage[s], [ZB] Z is —OH, Y is a lipophile group, $R_3$ and $R_4$ are acyl groups and $R_2$ is —$NH_2$.

14. The muramylpeptide of claim 13 wherein $R_3$ and $R_4$ are palmitoyl groups.

15. The muramylpeptide of claim 14 which is alpha(N-acetyl-muramyl-L-alanyl-D-isoglutamine), beta, gamma-dipalmitoyl-sn-glycerol.

16. The muramylpeptide of claim 14 which is alpha(N-acetyl-muramyl-D-alanyl-D-isoglutamine), beta, gamma-dipalmitoyl-sn-glycerol.

17. The muramylpeptide of claim 14 which is alpha(N-acetyl-muramyl-L-alanyl-D-isoglutaminyl-L-alanine), beta, gamma-dipalmitoyl-sn-glycerol.

18. The muramylpeptide of claim 14 which is alpha(N-acetyl-muramyl-D-alanyl-D-isoglutaminyl-L-alanine), beta, gamma-dipalmitoyl-sn-glycerol.

19. A pharmaceutical composition for stimulating the activity of macrophage which comprises a physiologically acceptable carrier and a macrophage stimulant effective amount of said muramylpeptide of claim 1.

20. A method for activating macrophages in a host which comprises the step of: administering to said host a macrophage activating amount said muramylpeptide of claim 1.

21. A method for stimulating anti-infectious activity of macrophages in a host which comprises administering to said host a macrophage stimulating amount of said muramylpeptide of claim 1.

22. A muramylpeptide of claim 1 having the formula:

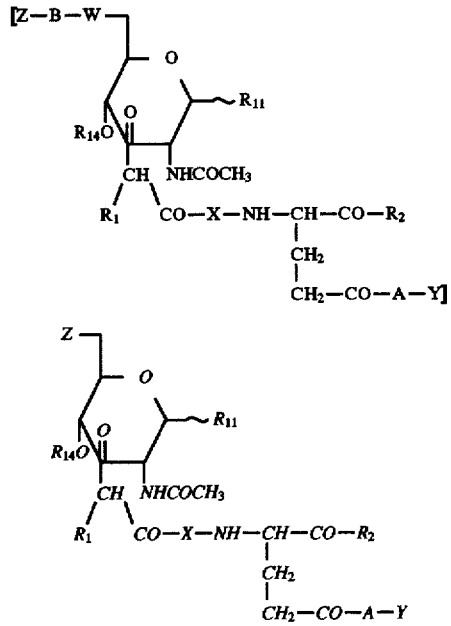

wherein:

$R_1$ is —H or —$CH_3$;

$R_2$ is —$NH_2$, —OH or —OD, with D being a hydrocarbon group of 1 to 10 carbon atoms;

$R_{11}$ is —OH;

[$R_1$] $R_{14}$ is —H;

X is an aminoacyl residue which is selected from the group consisting of alanyl, valyl, isoleucyl, norleucyl, leucyl, seryl, threonyl, prolyl, glutaminyl, asparaginyl, methionayl, tryptophanyl, phenylalanyl, tyrosyl and glycyl;

Y is —$NH_2$, —OH, —OD or a [—$OCH_2$—CH($R_3$)$CH_2$O($R_4$)] —*$OCH_2$—CH*($OR_3$)$CH_2O$($R_4$) lipophile group; $R_3$ and $R_4$ being identical or different and being individually an acyl lipophile group of 8 to 100 carbon atoms and D is as defined above;

Z is —$NH_2$, —OH, —OD or a [—CO—CHO($R_3$)$CH_2$O($R_4$)] —*OCO—CH*($OR_3$)$CH_2O$($R_4$) lipophile group; Y or Z or both being a lipophile group and D is as defined above;

[W is —O—;] and

A [and B are either] *is a* direct linkage[s] or bridging arm[s] which [are identical or different and which] comprises [individually] one to three aminoacyl residues, themselves identical or different from one another, said aminoacyl residues being selected from the group consisting of alanyl, valyl, isoleucyl, norleucyl, leucyl, seryl, threonyl, prolyl, glutaminyl, asparaginyl, methionyl, tryptophanyl, phenylalanyl, tyrosyl, and glycyl and which may be N-substituted by a lower alkyl group, or a —NH—$(CH_2)_p$—CO— group with p being an integer of 2 to 10.

* * * * *